US007141581B2

(12) United States Patent
Bender et al.

(10) Patent No.: US 7,141,581 B2
(45) Date of Patent: *Nov. 28, 2006

(54) INDAZOLE COMPOUNDS AND PHARMACEUTICAL COMPOSITIONS FOR INHIBITING PROTEIN KINASES, AND METHODS FOR THEIR USE

(75) Inventors: Steven Bender, Oceanside, CA (US); Dana Hu-Lowe, Encinitas, CA (US); David Ray Shalinsky, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 208 days.

This patent is subject to a terminal disclaimer.

(21) Appl. No.: 10/639,890

(22) Filed: Aug. 12, 2003

(65) Prior Publication Data
US 2005/0038097 A1    Feb. 17, 2005

Related U.S. Application Data

(60) Continuation-in-part of application No. 10/326,037, filed on Feb. 15, 2003, now Pat. No. 6,891,044, which is a division of application No. 09/983,783, filed on Oct. 25, 2001, now Pat. No. 6,534,524, which is a division of application No. 09/609,335, filed on Jun. 30, 2000, now abandoned.

(60) Provisional application No. 60/142,130, filed on Jul. 2, 1999.

(51) Int. Cl.
C07D 213/06 (2006.01)
A61K 31/4439 (2006.01)
A61K 31/416 (2006.01)

(52) U.S. Cl. ............... 514/314; 514/333; 514/338; 514/297; 546/152; 546/256; 546/275.7; 548/312.4

(58) Field of Classification Search ............ 546/152, 546/256, 275.7; 548/312.4; 514/314, 333, 514/338, 397
See application file for complete search history.

(56) References Cited

U.S. PATENT DOCUMENTS

| 5,621,082 | A | 4/1997 | Xiong et al. |
| 5,705,499 | A | 1/1998 | Cywin et al. |
| 5,760,028 | A | 6/1998 | Jadhav et al. |
| 5,861,414 | A | 1/1999 | Allen |
| 5,886,195 | A | 3/1999 | Tang et al. |
| 6,534,524 | B1 | 3/2003 | Kania et al. |

FOREIGN PATENT DOCUMENTS

| DE | 273 062 | 11/1989 |
| EP | 0 066 270 | 8/1982 |
| EP | 0 816 357 | 1/1998 |
| WO | WO 86/05779 | 10/1986 |
| WO | WO 93/19052 | 9/1993 |
| WO | WO 96/14843 | 5/1996 |
| WO | WO 96/23783 | 8/1996 |
| WO | WO 97/03967 | 2/1997 |
| WO | WO 97/16447 | 5/1997 |
| WO | WO 97/34876 | 9/1997 |
| WO | WO 97/48697 | 12/1997 |
| WO | WO 98/09961 | 3/1998 |
| WO | WO 98/14451 | 4/1998 |
| WO | WO 99/21845 | 5/1999 |
| WO | WO 99/23076 | 5/1999 |
| WO | WO 99/23077 | 5/1999 |
| WO | WO 00/18761 | 4/2000 |
| WO | WO00/37107 | 6/2000 |
| WO | WO00/38665 | 7/2000 |
| WO | WO00/38715 | 7/2000 |
| WO | WO00/38716 | 7/2000 |
| WO | WO00/38717 | 7/2000 |
| WO | WO00/38718 | 7/2000 |
| WO | WO00/38719 | 7/2000 |
| WO | WO00/38730 | 7/2000 |
| WO | WO00/38786 | 7/2000 |

OTHER PUBLICATIONS

Bertolini et al., "Endostatin, an antiangiogenic drug, induces tumor stabilitzation after chemotherapy . . . non-Hodgkin lumphoma," *Blood*, 2000, 96, 282-287.
Bruggen et al., "VEGR Antagonism Reduces Edema Formation and Tissue Damage after Ischemia/Reperfusion Injury in the Mouse Brain," 1999, 104; 1613-1620.
Monestiroli, Silva, "Kinetics and Viability of Circulating Endothelial Cells As Surrogate Angiogenesis Marker in an Animal Model of Human Lumphoma," *Cancer Research*, 2001, 61, 4341-4344.
Nasmyth, Kim, "Viewpoint: Putting the Cell Cycle in Order," *Science*, 1996, 274, 1643-1645.
Strawn et al., "Flk-1 as a target for tumor growth inhibition," *Cancer Research*, 1996, 56, 3540-3545.

(Continued)

*Primary Examiner*—Zinna N. Davis
(74) *Attorney, Agent, or Firm*—Matthew J. Pugmire; Bryan C. Zielinski

(57) ABSTRACT

Indazole compounds that modulate and/or inhibit the activity of certain protein kinases are described. These compounds and pharmaceutical compositions containing them are capable of mediating tyrosine kinase signal transduction and thereby modulate and/or inhibit unwanted cell proliferation. The invention is also directed to the therapeutic or prophylactic use of pharmaceutical compositions containing such compounds, and to methods of treating cancer and other disease states associated with unwanted angiogenesis and/or cellular proliferation, such as diabetic retinopathy, neovascular glaucoma, rheumatoid arthritis, and psoriasis, by administering effective amounts of such compounds.

11 Claims, No Drawings

OTHER PUBLICATIONS

Al-Khodairy et al., *Molec. Biol. Cell*, 5, 147-160 (1994).
Alon et. al, *Nat. Med.*, 1, 1024 (1995).
Bolen, *Oncogene*, 8, 2025-2031 (1993).
Bunz et al., *Science*, 282, 1497 (1998).
Castro et al., *J. Med Chem*, 39:842-849 (1996).
Cohen, *Curr. Op. Chem. Biol.*, 3, 459-65 (1999).
Folkman, *Nature Med.*, 1, 27-31 (1995).
Hartwell et al., *Science*, 266, 1821-1828 (1994).
Hartwell et al., *Science*, 246, 629-634 (1989).
Holash et al., *Oncogene*, 18, 5356-62 (1999).
Jeffrey et al., *Nature*, 376, 313-320 (Jul. 27, 1995).
Kamb, *Trends in Genetics*, 11, 136-140 (1995).
Kamb et al., *Science*, 264, 436-440 (1994).
Katsura et al., *Chem Pharm Biol*, 40(8), 2062-2074-140 (1992).
Klohs et al., *Curr. Op. Chem. Biol.*, 10, 544-49 (1999).
Klunder et al., *J. Med Chem*, 41, 2960-2971 (1998).
Lee et al., *Biochem*, 23, 4255 (1984).
Lin et al., *J Med Chem.*, 15(6), 615 (1972).
Lutty and McLeod, *Arch. Ophthalmol.*, 110, 267 (1992.
Maisonpierre et al., *Science*, 277, 55-60 (1997).
Matsuoka, *Science*, 282, 1893-1897 (1998).
McMahon et al., *Current Opinion in Drug Discovery & Development*, 1, 131-146 (1998).
McMahon et al, *Oncologist*, 5, 3-10 (2000).
Merenmines et al., *Cell Growth & Differentiation*, 8, 3-10 (1997).
Millauer et al., *Cancer Research*, 56, 1615-1620 (1996).
Mohammadi et al., *EMBO Journal*, 17, 5896-5904 (1998.
Mohammadi et al., *Mol. Cell. Biol.*, 16, 977-989 (1996).
Mylari et al., *J. Med. Chem.*, 35, 457-465 (1992).
Nurse, *Cell*, 91, 865-867 (1997).
O'Connor, *Cancer Surveys*, 29, 151-182 (1997).
Parast et al., *BioChemistry*, 37, 16788-16801 (1998).
Peng et al., *Science*, 277, 1501-1505 (1997).
Penn et al, *Invest. Ophthalmol. Vis. Sci.*, 36, 2063, (1995).
Rosenblatt et al., *J. Mol. Biol.*, 230, 1317-1319 (1993).
Rosowsky et al, *J. Med Chem.*, 31, 763-768 (1988).
Sanchez et al., *Science*. 277, 1497-1501 (1997).
Sarodnick et al, *J. Prakt. Chem. 339*, 714-720 (1997).
Still et al., *J. Org. Chem.*, 43, 2923 (1978).
Stone et al, *J. Neurosci.*, 15, 4738 (1995).
Strawn et al., *Exp. Opin. Invest. Drugs*, 7, 553-573 (1998).
Thomas et al., *J. Biol. Chem.*, 274, 36684-92 (1999).
Thompson, *Oncogene*, 15, 3025-3035 (1997).
Walworth et al., *Nature*, 363, 368-371 (1993).
Weinert, *Science*, 277, 1450-1451 (1997).
Whitney et al., DNA Cell Biol 9, 823-830, 1993.
Winters et al., *Oncogene*, 17, 673-684 (1998).
Yoshiji et al., *Cancer Research*, 57, 3924-3928 (1997).
Zeng et al., *Nature*, 395, 507-510 (1998).

INDAZOLE COMPOUNDS AND PHARMACEUTICAL COMPOSITIONS FOR INHIBITING PROTEIN KINASES, AND METHODS FOR THEIR USE

CROSS-REFERENCE TO RELATED APPLICATIONS

The present application is a continuation-in-part of application Ser. No. 10/326,037 filed Feb. 15, 2003 now U.S. Pat. No. 6,891,044, which is a divisional of application Ser. No. 09/983,783, filed Oct. 25, 2001, now U.S. Pat. No. 6,534,524, which is a divisional of application Ser. No. 09/609,335, filed Jun. 30, 2000, now abandoned, which claims the benefit of application Ser. No. 60/142,130, filed Jul. 2, 1999, the disclosures of which are incorporated herein by reference in their entireties.

FIELD OF THE INVENTION

This invention is directed to indazole compounds that mediate and/or inhibit the activity of certain protein kinases, and to pharmaceutical compositions containing such compounds. The invention is also directed to the therapeutic or prophylactic use of such compounds and compositions, and to methods of treating cancer as well as other disease states associated with unwanted angiogenesis and/or cellular proliferation, by administering effective amounts of such compounds.

BACKGROUND OF THE INVENTION

Protein kinases are a family of enzymes that catalyze phosphorylation of the hydroxyl group of specific tyrosine, serine, or threonine residues in proteins. Typically, such phosphorylation dramatically perturbs the function of the protein, and thus protein kinases are pivotal in the regulation of a wide variety of cellular processes, including metabolisim, cell proliferation, cell differentiation, and cell survival. Of the many different cellular functions in which the activity of protein kinases is known to be required, some processes represent attractive targets for therapeutic intervention for certain disease states. Two examples are angiogenesis and cell-cycle control, in which protein kinases play a pivotal role; these processes are essential for the growth of solid tumors as well as for other diseases.

Angiogenesis is the mechanism by which new capillaries are formed from existing vessels. When required, the vascular system has the potential to generate new capillary networks in order to maintain the proper functioning of tissues and organs. In the adult, however, angiogenesis is fairly limited, occurring only in the process of wound healing and neovascularization of the endometrium during menstruation. See Merenmies et al., *Cell Growth & Differentiation*, 8, 3–10 (1997). On the other hand, unwanted angiogenesis is a hallmark of several diseases, such as retinopathies, psoriasis, rheumatoid arthritis, age-related macular degeneration (AMD), and cancer (solid tumors). Folkman, *Nature Med.*, 1, 27–31 (1995). Protein kinases which have been shown to be involved in the angiogenic process include three members of the growth factor receptor tyrosine kinase family: VEGF-R2 (vascular endothelial growth factor receptor 2, also known as KDR (kinase insert domain receptor) and as FLK-1); FGF-R (fibroblast growth factor receptor); and TEK (also known as Tie-2).

VEGF-R2, which is expressed only on endothelial cells, binds the potent angiogenic growth factor VEGF and mediates the subsequent signal transduction through activation of its intracellular kinase activity. Thus, it is expected that direct inhibition of the kinase activity of VEGF-R2 will result in the reduction of angiogenesis even in the presence of exogenous VEGF (see Strawn et al., *Cancer Research*, 56, 3540–3545 (1996)), as has been shown with mutants of VEGF-R2 which fail to mediate signal transduction. Millauer et al., *Cancer Research*, 56, 1615–1620 (1996). Furthermore, VEGF-R2 appears to have no function in the adult beyond that of mediating the angiogenic activity of VEGF. Therefore, a selective inhibitor of the kinase activity of VEGF-R2 would be expected to exhibit little toxicity.

Similarly, FGF-R binds the angiogenic growth factors aFGF and bFGF and mediates subsequent intracellular signal transduction. Recently, it has been suggested that growth factors such as bFGF may play a critical role in inducing angiogenesis in solid tumors that have reached a certain size. Yoshiji et al., *Cancer Research*, 57, 3924–3928 (1997). Unlike VEGF-R2, however, FGF-R is expressed in a number of different cell types throughout the body and may or may not play important roles in other normal physiological processes in the adult. Nonetheless, systemic administration of a small-molecule inhibitor of the kinase activity of FGF-R has been reported to block bFGF-induced angiogenesis in mice without apparent toxicity. Mohammad et al., *EMBO Journal*, 17, 5996–5904 (1998).

TEK (also known as Tie-2) is another receptor tyrosine kinase expressed only on endothelial cells which has been shown to play a role in angiogenesis. The binding of the factor angiopoietin-1 results in autophosphorylation of the kinase domain of TEK and results in a signal transduction process which appears to mediate the interaction of endothelial cells with peri-endothelial support cells, thereby facilitating the maturation of newly formed blood vessels. The factor angiopoietin-2, on the other hand, appears to antagonize the action of angiopoietin-1 on TEK and disrupts angiogenesis. Maisonpierre et al., *Science*, 277, 55–60 (1997).

As a result of the above-described developments, it has been proposed to treat angiogenesis by the use of compounds inhibiting the kinase activity of VEGF-R2, FGF-R, and/or TEK. For example, WIPO International Publication No. WO 97/34876 discloses certain cinnoline derivatives that are inhibitors of VEGF-R2, which may be used for the treatment of disease states associated with abnormal angiogenesis and/or increased vascular permeability such as cancer, diabetes, psoriasis, rheumatoid arthritis, Kaposi's sarcoma, haemangioma, acute and chronic nephropathies, atheroma, arterial restinosis, autoimmune diseases, acute inflammation, and ocular diseases with retinal vessel proliferation.

Phosphorylase kinase activates glycogen phosphorylase, thus increasing glycogen breakdown and hepatic glucose release. Hepatic glucose production is disregulated in type 2 diabetes, and is the primary cause of fasting hyperglycemia, which results in many of the secondary complications afflicting these patients. Thus, reduction in glucose release from the liver would lower elevated plasma glucose levels. Inhibitors of phosphorylase kinase should therefore decrease phosphorylase activity and glycogenolysis, thus reducing hyperglycemia in patients.

Another physiological response to VEGF is vascular hyperpermeability, which has been proposed to play a role in the early stages of angiogenesis. In ischemic tissues, such as those occurring in the brain of stroke victims, hypoxia trigger VEGF expression, leading to increased vascular permeability and ultimately edema in the surrounding tissues. In a rat model for stroke, it has been shown by van Bruggen et al., *J. Clinical Invest*, 104, 1613–20 (1999) that administration of a monoclonal antibody to VEGF reduces the infarct volume. Thus, inhibitors of VEGFR are anticipated to be useful for the treatment of stroke.

In addition to its role in angiogenesis, protein kinases also play a crucial role in cell-cycle control. Uncontrolled cell proliferation is the insignia of cancer. Cell proliferation in response to various stimuli is manifested by a de-regulation of the cell division cycle, the process by which cells multiply and divide. Tumor cells typically have damage to the genes that directly or indirectly regulate progression through the cell division cycle.

Cyclin-dependent kinases (CDKs) are serine-threonine protein kinases that play critical roles in regulating the transitions between different phases of the cell cycle. See, e.g., the articles compiled in *Science*, 274, 1643–1677 (1996). CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific phases of the cell cycle.

It is CDK4 complexed to the D cyclins that plays a critical part in initiating the cell-division cycle from a resting or quiescent stage to one in which cells become committed to cell division. This progression is subject to a variety of growth regulatory mechanisms, both negative and positive. Aberrations in this control system, particularly those that affect the function of CDK4, have been implicated in the advancement of cells to the highly proliferative state characteristic of malignancies, particularly familial melanomas, esophageal carcinomas, and pancreatic cancers. See, e.g., Kamb, *Trends in Genetics*, 11, 136–140 (1995); Kamb et al., *Science*, 264, 436–440 (1994).

Myriad publications describe a variety of chemical compounds useful against a variety of therapeutic targets. For example, WIPO International Publication Nos. WO 99/23077 and WO 99/23076 describe indazole-containing compounds having phosphodiesterase type IV inhibitory activity produced by an indazole-for-catechol bioisostere replacement. U.S. Pat. No. 5,760,028 discloses heterocycles including 3-[1-[3-(imidazolin-2-ylamino)propyl]indazol-5-ylcarbonylamino]-2-(benzyloxycarbonylamino)propionic acid, which are useful as antagonists of the $\alpha_v\beta_3$ integrin and related cell surface adhesive protein receptors. WIPO International Publication No. WO 98/09961 discloses certain indazole derivatives and their use as inhibitors of phosphodiesterase (PDE) type IV or the production of tumor necrosis factor (TNF) in a mammal. Recent additions to the virtual library of known compounds include those described as being anti-proliferative therapeutic agents that inhibit CDKs. For example, U.S. Pat. No. 5,621,082 to Xiong et al. discloses nucleic acid encoding an inhibitor of CDK6, and European Patent Publication No. 0 666 270 A2 describes peptides and peptide mimetics that act as inhibitors of CDK1 and CDK2. WIPO International Publication No. WO 97/16447 discloses certain analogs of chromones that are inhibitors of cyclin-dependent kinases, in particular of CDK/cyclin complexes such as CDK4/cyclin D1, which may be used for inhibiting excessive or abnormal cell proliferation, and therefore for treating cancer. WIPO International Publication No. WO 99/21845 describes 4-aminothiazole derivatives that are useful as CDK inhibitors.

There is still a need, however, for small-molecule compounds that may be readily synthesized and are effective in inhibiting one or more CDKs or CDK/cyclin complexes. Because CDK4 may serve as a general activator of cell division in most cells, and complexes of CDK4 and D-type cyclins govern the early $G_1$ phase of the cell cycle, there is a need for effective inhibitors of CDK4, and D-type cyclin complexes thereof, for treating one or more types of tumors. Also, the pivotal roles of cyclin E/CDK2 and cyclin B/CDK1 kinases in the $G_1$/S phase and $G_2$/M transitions, respectively, offer additional targets for therapeutic intervention in suppressing deregulated cell-cycle progression in cancer.

Another protein kinase, CHK1, plays an important role as a checkpoint in cell-cycle progression. Checkpoints are control systems that coordinate cell-cycle progression by influencing the formation, activation and subsequent inactivation of the cyclin-dependent kinases. Checkpoints prevent cell-cycle progression at inappropriate times, maintain the metabolic balance of cells while the cell is arrested, and in some instances can induce apoptosis (programmed cell death) when the requirements of the checkpoint have not been met. See, e.g., O'Connor, *Cancer Surveys*, 29, 151–182 (1997); Nurse, *Cell*, 91, 865–867 (1997); Hartwell et al., *Science*, 266, 1821–1828 (1994); Hartwell et al., *Science*, 246, 629–634 (1989).

One series of checkpoints monitors the integrity of the genome and, upon sensing DNA damage, these "DNA damage checkpoints" block cell-cycle progression in $G_1$ and $G_2$ phases, and slow progression through S phase. O'Connor, *Cancer Surveys*, 29, 151–182 (1997); Hartwell et al., *Science*, 266, 1821–1828 (1994). This action enables DNA repair processes to complete their tasks before replication of the genome and subsequent separation of this genetic material into new daughter cells takes place. Importantly, the most commonly mutated gene in human cancer, the p53 tumor suppressor gene, produces a DNA damage checkpoint protein that blocks cell-cycle progression in $G_1$ phase and/or induces apoptosis (programmed cell death) following DNA damage. Hartwell et al., *Science*, 266, 1821–1828 (1994). The p53 tumor suppressor has also been shown to strengthen the action of a DNA damage checkpoint in $G_2$ phase of the cell cycle. See, e.g., Bunz et al., *Science*, 28, 1497–1501 (1998); Winters et al., *Oncogene*, 17, 673–684 (1998); Thompson, *Oncogene*, 15, 3025–3035 (1997).

Given the pivotal nature of the p53 tumor suppressor pathway in human cancer, therapeutic interventions that exploit vulnerabilities in p53-defective cancer have been actively sought. One emerging vulnerability lies in the operation of the $G_2$ checkpoint in p53 defective cancer cells. Cancer cells, because they lack $G_1$ checkpoint control, are particularly vulnerable to abrogation of the last remaining barrier protecting them from the cancer-killing effects of DNA-damaging agents: the $G_2$ checkpoint. The $G_2$ checkpoint is regulated by a control system that has been conserved from yeast to humans. Important in this conserved system is a kinase, CHK1, which transduces signals from the DNA-damage sensory complex to inhibit activation of the cyclin B/Cdc2 kinase, which promotes mitotic entry. See, e.g., Peng et al., *Science*, 277, 1501–1505 (1997); Sanchez et al., *Science*, 277, 1497–1501 (1997). Inactivation of CHK1 has been shown to both abrogate $G_2$ arrest induced by DNA damage inflicted by either anticancer agents or endogenous DNA damage, as well as result in preferential killing of the resulting checkpoint defective cells. See, e.g., Nurse, *Cell*, 91, 865–867 (1997); Weinert, *Science*, 277, 1450–1451

(1997); Walworth et al., *Nature*, 363, 368–371 (1993); and Al-Khodairy et al., *Molec. Biol. Cell*, 5, 147–160 (1994).

Selective manipulation of checkpoint control in cancer cells could afford broad utilization in cancer chemotherapeutic and radiotherapy regimens and may, in addition, offer a common hallmark of human cancer "genomic instability" to be exploited as the selective basis for the destruction of cancer cells. A number of factors place CHK1 as a pivotal target in DNA-damage checkpoint control. The elucidation of inhibitors of this and functionally related kinases such as Cds1/CHK2, a kinase recently discovered to cooperate with CHK1 in regulating S phase progression (see Zeng et al., *Nature*, 395, 507–510 (1998); Matsuoka, *Science*, 282, 1893–1897 (1998)), could provide valuable new therapeutic entities for the treatment of cancer.

Integrin receptor binding to ECM initiates intracellular signals mediated by FAK (Focal Adhesion Kinase) that are involved in cell motility, cellular proliferation, and survival. In human cancers, FAK overexpression is implicated in tumorigenesis and metastatic potential through its role in integrin mediated signaling pathways.

Tyrosine kinases can be of the receptor type (having extracellular, transmembrane and intracellular domains) or the non-receptor type (being wholly intracellular). At least one of the non-receptor protein tyrosine kinases, namely, LCK, is believed to mediate the transduction in T-cells of a signal from the interaction of a cell-surface protein (Cd4) with a cross-linked anti-Cd4 antibody. A more detailed discussion of non-receptor tyrosine kinases is provided in Bolen, *Oncogene*, 8, 2025–2031 (1993), which is incorporated herein by reference.

In addition to the protein kinases identified above, many other protein kinases have been considered to be therapeutic targets, and numerous publications disclose inhibitors of kinase activity, as reviewed in the following: McMahon et al, *Oncologist*, 5, 3–10 (2000); Holash et al., *Oncogene*, 18, 5356–62 (1999); Thomas et al., *J. Biol. Chem.*, 274, 36684–92 (1999); Cohen, *Curr. Op. Chem. Biol.*, 3, 459–65 (1999); Klohs et al., *Curr. Op. Chem. Biol.*, 10, 544–49 (1999); McMahon et al., *Current Opinion in Drug Discovery & Development*, 1, 131–146 (1998); Strawn et al., *Exp. Opin. Invest. Drugs*, 7, 553–573 (1998). WIPO International Publication WO 00/18761 discloses certain substituted 3-cyanoquinolines as protein kinase inhibitors.

There is still a need, however, for effective inhibitors of protein kinases. Moreover, as is understood by those skilled in the art, it is desirable for kinase inhibitors to possess both high affinity for the target kinase or kinases as well as high selectivity versus other protein kinases.

SUMMARY OF THE INVENTION

Thus, an objective of the invention is to discover potent inhibitors of protein kinases. Another objective of the invention is to discover effective kinase inhibitors having a strong and selective affinity for one or more particular kinases.

These and other objectives of the invention, which will become apparent from the following description, have been achieved by the discovery of the indazole compounds, pharmaceutically acceptable prodrugs, pharmaceutically active metabolites, and pharmaceutically acceptable salts thereof (such compounds, prodrugs, metabolites and salts are collectively referred to as "agents") described below, which modulate and/or inhibit the activity of protein kinases. Pharmaceutical compositions containing such agents are useful in treating diseases mediated by kinase activity, such as cancer, as well as other disease states associated with unwanted angiogenesis and/or cellular proliferation, such as diabetic retinopathy, neovascular glaucoma, rheumatoid arthritis, and psoriasis. Further, the agents have advantageous properties relating to the modulation and/or inhibition of the kinase activity associated with VEGF-R, FGF-R, CDK complexes, CHK1, LCK, TEK, FAK, and/or phosphorylase kinase.

In a general aspect, the invention relates to compounds of the Formula I:

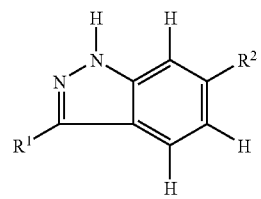

wherein:

$R^1$ is a substituted or unsubstituted aryl or heteroaryl, or a group of the formula $CH=CH-R^3$ or $CH=N-R^3$ where $R^3$ is a substituted or unsubstituted alkyl, alkenyl, cycloalkyl, heterocycloalkyl, aryl, or heteroaryl; and $R^2$ is a substituted or unsubstituted aryl, heteroaryl, or Y—X, where Y is O, S, $C=CH_2$, C=O, S=O, $SO_2$, alkylidene, NH, or N—($C_1$–$C_8$ alkyl), and X is substituted or unsubstituted Ar, heteroaryl, NH-(alkyl), NH-(cycloalkyl), NH-(heterocycloalkyl), NH(aryl), NH(heteroaryl), NH-(alkoxyl), or NH-(dialkylamide), where Ar is aryl;

The invention is also directed to pharmaceutically acceptable prodrugs, pharmaceutically active metabolites, and pharmaceutically acceptable salts of the compounds of Formula I. Advantageous methods of making the compounds of the Formula I are also described.

In another general aspect, the invention relates to compounds of the Formula I(a):

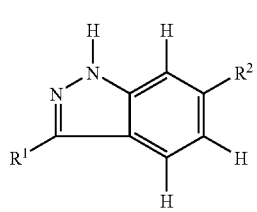

wherein:

$R^1$ is a substituted or unsubstituted aryl or heteroaryl, or a group of the formula $CH=CH-R^3$ or $CH=N-R^3$ where $R^3$ is a substituted or unsubstituted alkyl, alkenyl, cycloalkyl, heterocycloalkyl, aryl, or heteroaryl; and $R^2$ is a substituted or unsubstituted aryl or Y—Ar, where Y is O, S, $C=CH_2$, C=O, S=O, $SO_2$, $CH_2$, $CHCH_3$, NH, or N—($C_1$–$C_8$ alkyl), and Ar is a substituted or unsubstituted aryl.

The invention is also directed to pharmaceutically acceptable prodrugs, pharmaceutically active metabolites, and pharmaceutically acceptable salts of the compounds of Formula I(a). Advantageous methods of making the compounds of the Formula I(a) are also described.

In one preferred general embodiment, the invention relates to compounds having the Formula II:

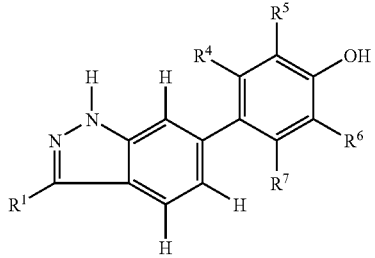

wherein:

$R^1$ is a substituted or unsubstituted aryl or heteroaryl, or a group of the formula CH=CH—$R^3$ or CH=N—$R^3$, where $R^3$ is a substituted or unsubstituted alkyl, cycloalkyl, heterocycloalkyl, aryl, or heteroaryl;

$R^4$ and $R^7$ are each independently hydrogen, OH, halo, $C_1$–$C_8$ alkyl, $C_1$–$C_8$ alkoxy, $C_1$–$C_8$ alkenyl, aryloxy, thioaryl, $CH_2$—OH, $CH_2$—O—($C_1$–$C_8$ alkyl), $CH_2$—O-aryl, $CH_2$—S—($C_1$–$C_8$alkyl), or $CH_2$—S-aryl;

$R^5$ and $R^6$ are each independently hydrogen, OH, halo, Z-alkyl, Z-aryl, or Z-$CH_2$CH=$CH_2$, where Z is O, S, NH, or $CH_2$, and the alkyl and aryl moieties of Z-alkyl and Z-aryl are each optionally substituted;

and pharmaceutically acceptable prodrugs, pharmaceutically active metabolites, and pharmaceutically acceptable salts thereof.

In a preferred embodiment of Formula II: $R^1$ is a substituted or unsubstituted bicyclic heteroaryl, or a group of the formula CH=CH—$R^3$ where $R^3$ is a substituted or unsubstituted aryl or heteroaryl; $R^4$ and $R^7$ are each independently hydrogen or $C_1$–$C_8$ alkyl; and $R^5$ and $R^6$ are each independently halo, Z-alkyl, or Z-$CH_2$CH=$CH_2$, where Z is O or S.

In another preferred general embodiment, compounds of the invention are of Formula III:

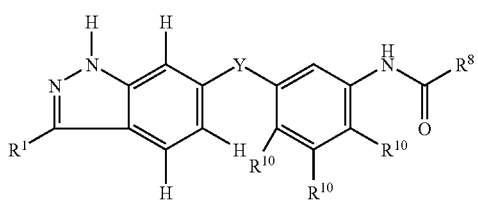

wherein:

$R^1$ is a substituted or unsubstituted aryl or heteroaryl, or a group of the formula CH=CH—$R^3$ or CH=N—$R^3$, where $R^3$ is a substituted or unsubstituted alkyl, cycloalkyl, heterocycloalkyl, aryl, or heteroaryl;

Y is O, S, C=$CH_2$, C=O, S=O, $SO_2$, $CH_2$, $CHCH_3$, NH, or N—($C_1$–$C_8$ alkyl);

$R^8$ is a substituted or unsubstituted alkyl, alkenyl, cycloalkyl, heterocycloalkyl, aryl, heteroaryl, alkoxyl, or aryloxyl;

$R^{10}$ is independently selected from hydrogen, halogen, and lower-alkyl;

and pharmaceutically acceptable prodrugs, pharmaceutically acceptable metabolites, and pharmaceutically acceptable salts thereof.

More preferably, in Formula III: $R^1$ is a substituted or unsubstituted bicyclic heteroaryl, or a group of the formula CH=CH—$R^3$ where $R^3$ is a substituted or unsubstituted aryl or heteroaryl; Y is O, S, C=$CH_2$, C=O, NH, or N—($C_1$–$C_8$ alkyl); $R^8$ is a substituted or unsubstituted aryl, heteroaryl, alkyl, and alkenyl, and $R^{10}$ is hydrogen or halogen.

In another preferred general embodiment, compounds of the invention are of Formula III(a):

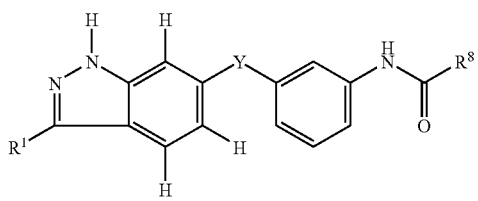

wherein:

$R^1$ is a substituted or unsubstituted aryl or heteroaryl, or a group of the formula CH=CH—$R^3$ or CH=N—$R^3$, where $R^3$ is a substituted or unsubstituted alkyl, cycloalkyl, heterocycloalkyl, aryl, or heteroaryl;

Y is O, S, C=$CH_2$, C=O, S=O, $SO_2$, $CH_2$, $CHCH_3$, NH, or N—($C_1$–$C_8$ alkyl);

$R^8$ is a substituted or unsubstituted alkyl, alkenyl, cycloalkyl, heterocycloalkyl, aryl, heteroaryl, alkoxyl, or aryloxyl;

and pharmaceutically acceptable prodrugs, pharmaceutically acceptable metabolites, and pharmaceutically acceptable salts thereof.

More preferably, in Formula III(a): $R^1$ is a substituted or unsubstituted bicyclic heteroaryl, or a group of the formula CH=CH—$R^3$ where $R^3$ is a substituted or unsubstituted aryl or heteroaryl; Y is O, S, C=$CH_2$, C=O, NH, or N—($C_1$–$C_8$ alkyl); and $R^8$ is a substituted or unsubstituted aryl or heteroaryl.

In another preferred general embodiment, compounds of the invention are of Formula IV:

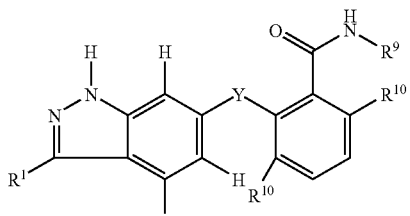

wherein:

$R^1$ is a substituted or unsubstituted aryl or heteroaryl, or a group of the formula CH=CH—$R^3$ or CH=N—$R^3$, where $R^3$ is a substituted or unsubstituted alkyl, cycloalkyl, heterocycloalkyl, aryl, or heteroaryl;

Y is O, S, C=$CH_2$, C=O, S=O, $SO_2$, $CH_2$, $CHCH_3$, NH, or N—($C_1$–$C_8$ alkyl);

$R^9$ is a substituted or unsubstituted alkyl, cycloalkyl, heterocycloalkyl, aryl, heteroaryl, alkoxyl, aryloxyl, cycloalkoxyl, NH—($C_1$–$C_8$ alkyl), NH-(aryl), NH-(heteroaryl), N=CH-(alkyl), NH(C=O)$R^{11}$, or $NH_2$, where $R^{11}$ is independently selected from hydrogen, substituted or unsubstituted alkyl, cycloalkyl, heterocycloalkyl, aryl, and heteroaryl; and $R^{10}$ is independently selected from hydrogen, halogen, and lower-alkyl;

and pharmaceutically acceptable prodrugs, pharmaceutically acceptable metabolites, and pharmaceutically acceptable salts thereof.

More preferably, in Formula IV: $R^1$ is a group of the formula CH=CH—$R^3$ where $R^3$ is a substituted or unsubstituted aryl or heteroaryl; Y is S or NH, and $R^9$ is a substituted or unsubstituted alkyl, alkoxyl, or NH-(heteroaryl).

Most preferred are compounds of the invention selected from:

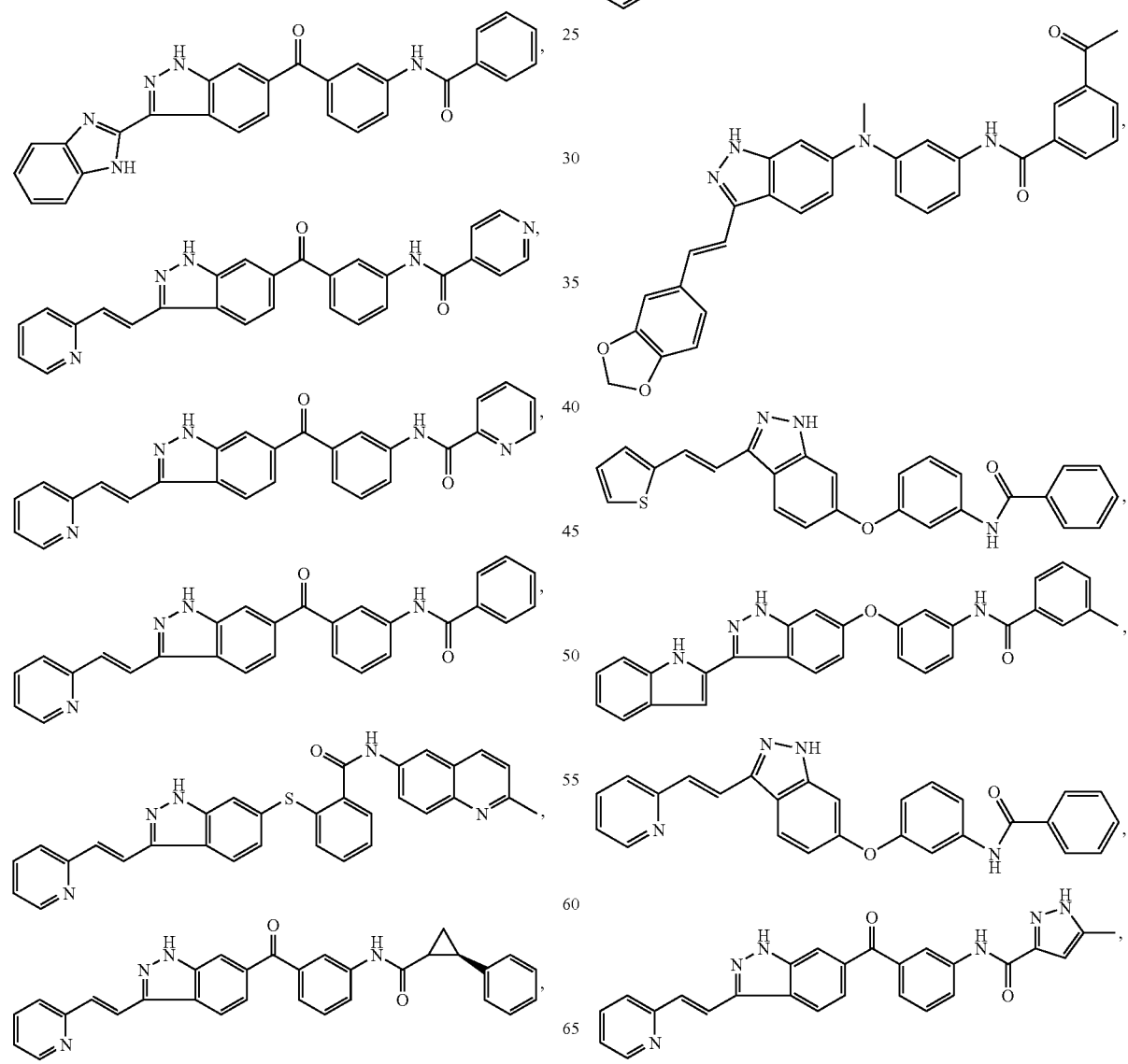

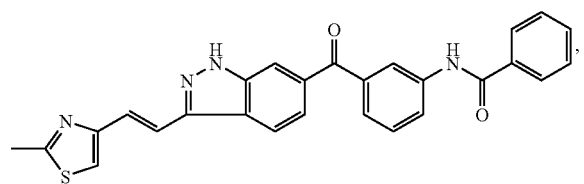
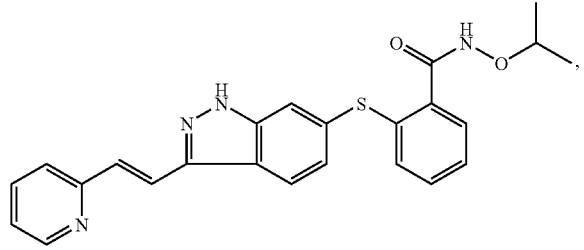
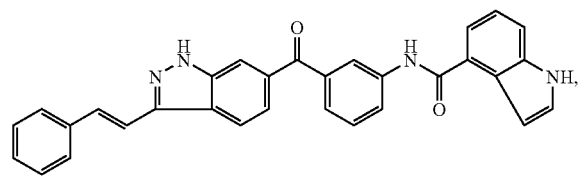
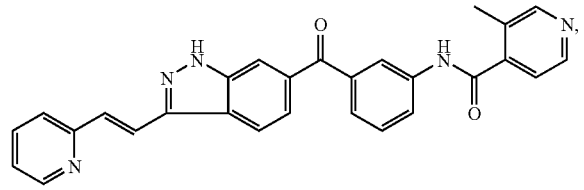
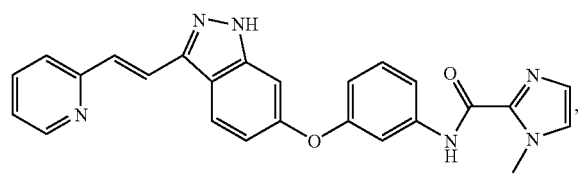
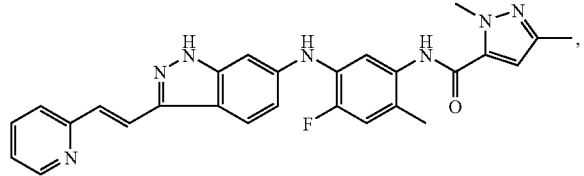
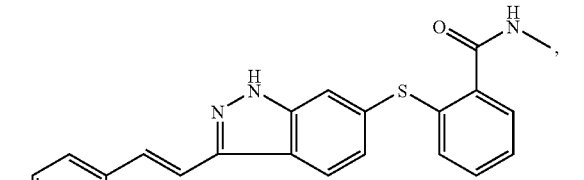
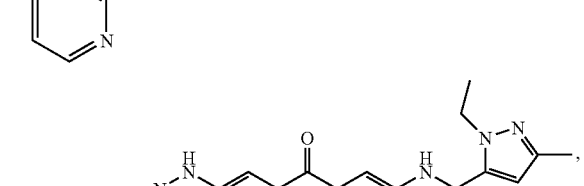
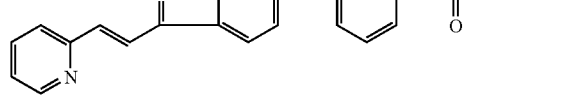
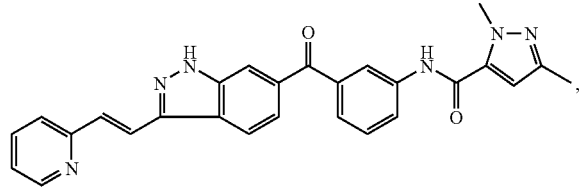
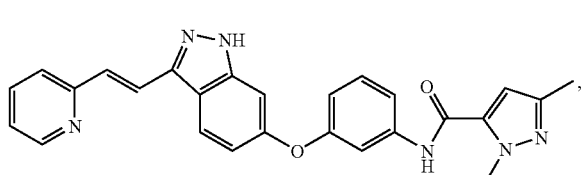
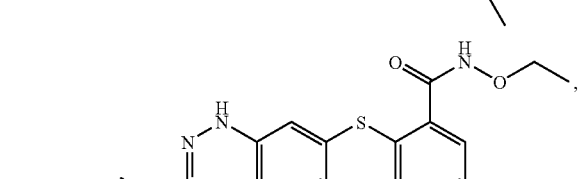
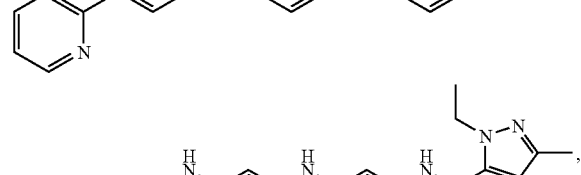
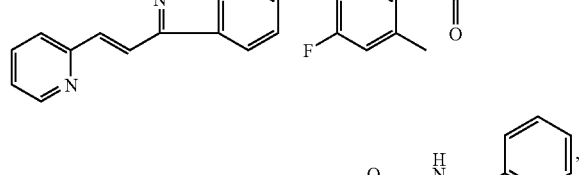
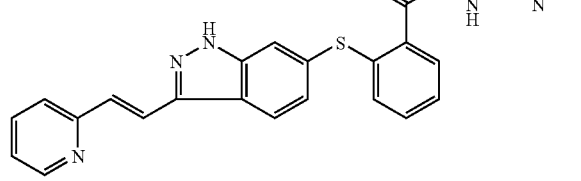
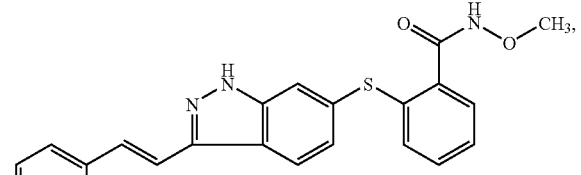
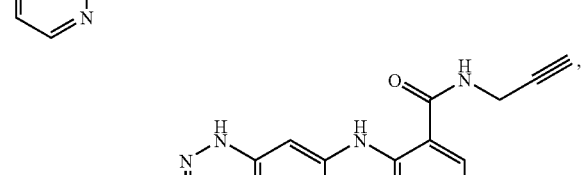
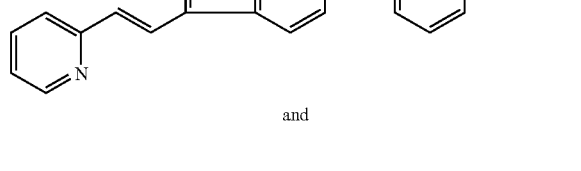
and -continued

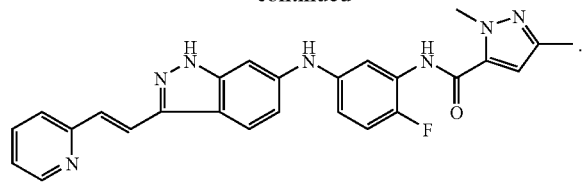

5

The invention also relates to a method of modulating and/or inhibiting the kinase activity of VEGF-R, FGF-R, a CDK complex, CHK1, LCK, TEK, FAK, and/or phosphorylase kinase by administering a compound of the Formula I, II, III, or IV, or a pharmaceutically acceptable prodrug, pharmaceutically active metabolite, or pharmaceutically acceptable salt thereof. Preferred compounds of the present invention that have selective kinase activity—i.e., they possess significant activity against one or more specific kinases while possessing less or minimal activity against one or more different kinases. In one preferred embodiment of the invention, compounds of the present invention are those of Formula I possessing substantially higher potency against VEGF receptor tyrosine kinase than against FGF-R1 receptor tyrosine kinase. The invention is also directed to methods of modulating VEGF receptor tyrosine kinase activity without significantly modulating FGF receptor tyrosine kinase activity.

The inventive compounds may be used advantageously in combination with other known therapeutic agents. For example, compounds of Formula I, II, III, or IV which possess antiangiogenic activity, including lymphangiogenic activity, may be co-administered with cytotoxic chemotherapeutic agents, such as taxol, taxotere, vinblastine, cis-platin, doxorubicin, adriamycin, and the like, to produce an enhanced antitumor effect. Additive or synergistic enhancement of therapeutic effect may also be obtained by co-administration of compounds of Formula I, II, III, or IV which possess antiangiogenic activity, including lymphangiogenic activity, with other antiangiogenic agents, such as combretastatin A-4, endostatin, prinomastat, celecoxib, rofocoxib, EMD121974, IM862, anti-VEGF monoclonal antibodies, and anti-KDR monoclonal antibodies.

The invention also relates to pharmaceutical compositions, each comprising an effective amount of an agent selected from compounds of Formula I and pharmaceutically acceptable salts, pharmaceutically active metabolites, and pharmaceutically acceptable prodrugs thereof; and a pharmaceutically acceptable carrier or vehicle for such agent.

The invention further provides methods of treating cancer as well as other disease states associated with unwanted angiogenesis, including lymphangiogenesis, and/or cellular proliferation, comprising administering effective amounts of such an agent to a patient in need of such treatment.

In one embodiment, the invention provides a method of treating a hyperproliferative disorder in a mammal, including a human, by administering to the mammal a therapeutically effective amount of a composition comprising a compound of formula I:

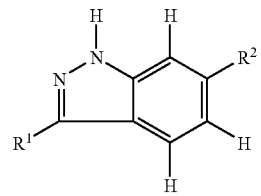

I wherein $R^1$ and $R^2$ are as defined above, or pharmaceutically acceptable prodrugs, pharmaceutically active metabolites, and pharmaceutically acceptable salts thereof, and a pharmaceutically acceptable carrier.

In a particular aspect of this embodiment, the hyperproliferative disorder is cancer, such as, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and combinations thereof.

In another particular aspect of this embodiment, the hyperproliferative disorder is a noncancerous hyperproliferative disorder, such as, but not limited to, a benign hyperplasia of the skin or prostate.

Optionally, the method further includes administering to the mammal an anti-tumor agent selected from the group consisting of mitotic inhibitors, alkylating agents, antimetabolites, intercalating antibiotics, growth factor inhibitors, cell cycle inhibitors, enzymes, topoisomerase inhibitors, biological response modifiers, antibodies, cytotoxics, anti-hormones, anti-androgens, and mixtures thereof.

In another embodiment, the present invention provides a method of treating pancreatitis or kidney disease in a mammal, including a human, by administering to the mammal a therapeutically effective amount of a composition comprising a compound of formula I:

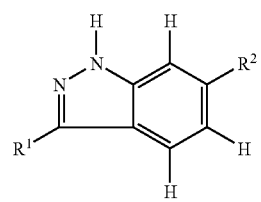

I wherein $R^1$ and $R^2$ are as defined above, or pharmaceutically acceptable prodrugs, pharmaceutically active metabolites, and pharmaceutically acceptable salts thereof, and a pharmaceutically acceptable carrier.

In another embodiment, the invention provides a method of preventing blastocyte implantation in a mammal, including a human, by administering to the mammal a therapeutically effective amount of a composition comprising a compound of formula I:

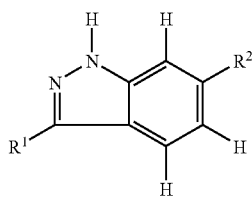

wherein R¹ and R² are as defined above, or pharmaceutically acceptable prodrugs, pharmaceutically active metabolites, and pharmaceutically acceptable salts thereof, and a pharmaceutically acceptable carrier.

In another embodiment, the invention provides a method for treating a disease related to vasculogenesis or angiogenesis in a mammal, including a human, by administering to the mammal a therapeutically effective amount of a composition comprising a compound of formula I:

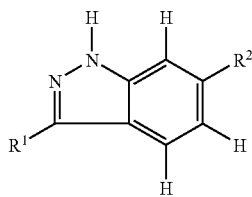

wherein R¹ and R² are as defined above, or pharmaceutically acceptable prodrugs, pharmaceutically active metabolites, and pharmaceutically acceptable salts thereof, and a pharmaceutically acceptable carrier.

In a particular aspect of this embodiment, the disease is selected from the group consisting of tumor angiogenesis, chronic inflammatory disease, atherosclerosis, skin diseases, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer. Optionally, the method further includes administering to the mammal a therapeutically effective amount of an anti-hypertensive agent.

In another embodiment, the invention provides a method of inhibiting circulating progenitor endothelial cell (CEP) and/or circulating endothelial cell (CEC) growth, by administering to a mammal, including a human, a therapeutically effective amount of a composition comprising a compound of formula I:

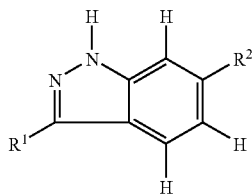

wherein R¹ and R² are as defined above, or pharmaceutically acceptable prodrugs, pharmaceutically active metabolites, and pharmaceutically acceptable salts thereof, and a pharmaceutically acceptable carrier. Preferably, the composition is administered in combination with chemotherapy to prevent or inhibit a rebound of CEP growth.

In further specific embodiments of any of the inventive methods described herein, the method further comprises administering to the mammal an amount of one or more substances selected from anti-tumor agents, anti-angiogenesis agents, signal transduction inhibitors, and antiproliferative agents, which amounts are together effective in treating said abnormal cell growth. Such substances include those disclosed in PCT publication nos. WO 00/38715, WO 00/38716, WO 00/38717, WO 00/38718, WO 00/38719, WO 00/38730, WO 00/38665, WO 00/37107 and WO 00/38786, the disclosures of which are incorporated herein by reference in their entireties.

In a preferred aspect of any of the method of treating embodiments, the compound of formula I is selected from:

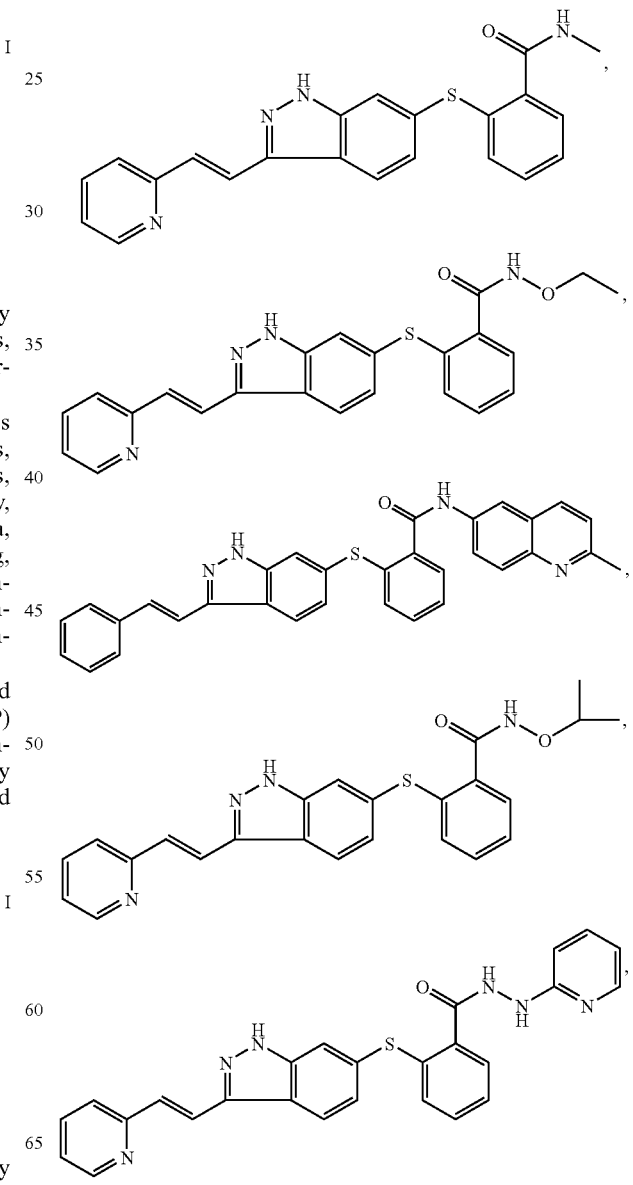

-continued

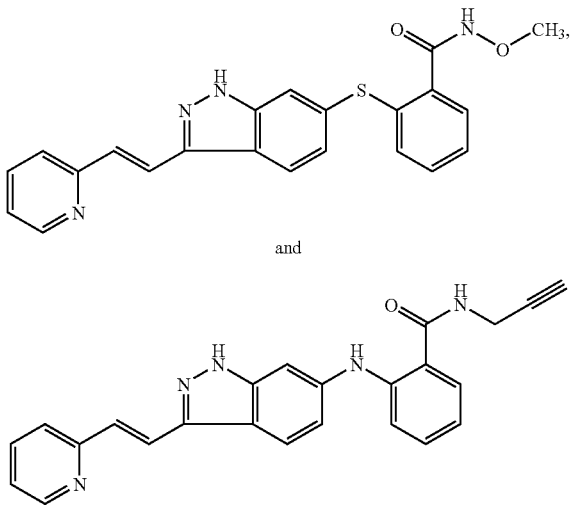

and

DETAILED DESCRIPTION OF INVENTION AND PREFERRED EMBODIMENTS

The inventive compounds of the Formula I, II, III, and IV are useful for mediating the activity of protein kinases. More particularly, the compounds are useful as anti-angiogenesis agents and as agents for modulating and/or inhibiting the activity of protein kinases, thus providing treatments for cancer or other diseases associated with cellular proliferation mediated by protein kinases.

The term "alkyl" as used herein refers to straight- and branched-chain alkyl groups having one to twelve carbon atoms. Exemplary alkyl groups include methyl (Me), ethyl (Et), n-propyl, isopropyl, butyl, isobutyl, sec-butyl, tert-butyl (t-Bu), pentyl, isopentyl, tert-pentyl, hexyl, isohexyl, and the like. The term "lower alkyl" designates an alkyl having from 1 to 8 carbon atoms (a $C_{1-8}$-alkyl). Suitable substituted alkyls include fluoromethyl, difluoromethyl, trifluoromethyl, 2-fluoroethyl, 3-fluoropropyl, hydroxymethyl, 2-hydroxyethyl, 3-hydroxypropyl, and the like.

The term "alkylidene" refers to a divalent radical having one to twelve carbon atoms. Illustrative alkylidene groups include $CH_2$, $CHCH_3$, $(CH_3)_2$, and the like.

The term "alkenyl" refers to straight- and branched-chain alkenyl groups having from two to twelve carbon atoms. Illustrative alkenyl groups include prop-2-enyl, but-2-enyl, but-3-enyl, 2-methylprop-2-enyl, hex-2-enyl, and the like.

The term "alkynyl" refers to straight- and branched-chain alkynyl groups having from two to twelve carbon atoms.

The term "cycloalkyl" refers to saturated or partially unsaturated carbocycles having from three to twelve carbon atoms, including bicyclic and tricyclic cycloalkyl structures. Suitable cycloalkyls include cyclopropyl, cyclobutyl, cyclopentyl, cyclohexyl, cycloheptyl, and the like.

A "heterocycloalkyl" group is intended to mean a saturated or partially unsaturated monocyclic radical containing carbon atoms, preferably 4 or 5 ring carbon atoms, and at least one heteroatom selected from nitrogen, oxygen and sulfur.

The terms "aryl" and "heteroaryl" refer to monocyclic and polycyclic unsaturated or aromatic ring structures, with "aryl" referring to those that are carbocycles and "heteroaryl" referring to those that are heterocycles. Examples of aromatic ring structures include phenyl, naphthyl, 1,2,3,4-tetrahydronaphthyl, furyl, thienyl, pyrrolyl, pyridinyl, pyrazolyl, imidazolyl, pyrazinyl, pyridazinyl, 1,2,3-triazinyl, 1,2,4-oxadiazolyl, 1,3,4-oxadiazolyl, 1-H-tetrazol-5-yl, indolyl, quinolinyl, benzofuranyl, benzothiophenyl (thianaphthenyl), and the like. Such moieties may be optionally substituted by a fused-ring structure or bridge, for example $OCH_2$—O.

The term "alkoxy" is intended to mean the radical —O-alkyl. Illustrative examples include methoxy, ethoxy, propoxy, and the like.

The term "aryloxy" respresents —O-aryl, wherein aryl is defined above.

The term "cycloalkoxyl" represents —O-cycloalkyl, wherein cycloalkyl is defined above.

The term "halogen" represents chlorine, fluorine, bromine or iodine. The term "halo" represents chloro, fluoro, bromo or iodo.

In general, the various moieties or functional groups for variables in the formulae may be optionally substituted by one or more suitable substituents. Exemplary substituents include a halogen (F, Cl, Br, or I), lower alkyl, —OH, —$NO_2$, —CN, —$CO_2H$, —O-lower alkyl, -aryl, -aryl-lower alkyl, —$CO_2CH_3$, —$CONH_2$, —$OCH_2CONH_2$, —$NH_2$, —$SO_2NH_2$, haloalkyl (e.g., —$CF_3$, —$CH_2CF_3$), —O-haloalkyl (e.g., —$OCF_3$, —$OCHF_2$), and the like.

The terms "comprising" and "including" are used in an open, non-limiting sense.

It is understood that while a compound of Formula I may exhibit the phenomenon of tautomerism, the formula drawings within this specification expressly depict only one of the possible tautomeric forms. It is therefore to be understood that within the invention the formulae are intended to represent any tautomeric form of the depicted compound and is not to be limited merely to a specific tautomeric form depicted by the formula drawings.

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulas are intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of the Formula I, II, III, and IV, the invention includes pharmaceutically acceptable prodrugs, pharmaceutically active metabolites, and pharmaceutically acceptable salts of such compounds.

"A pharmaceutically acceptable prodrug" is a compound that may be converted under physiological conditions or by solvolysis to the specified compound or to a pharmaceutically acceptable salt of such compound.

"A pharmaceutically active metabolite" is intended to mean a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. See, e.g., Bertolini, G. et al., *J. Med. Chem.*, 40, 2011–2016 (1997); Shan, D. et al., *J. Pharm. Sci.*, 86 (7), 765–767; Bagshawe K., *Drug Dev. Res.*, 34, 220–230 (1995); Bodor, N., *Advances in Drug Res.*, 13, 224–331 (1984); Bundgaard, H., *Design of Prodrugs* (Elsevier Press 1985); and Larsen, I. K., *Design and Application of Prodrugs*, Drug Design and Development (Krogsgaard-Larsen et al., eds., Harwood Academic Publishers, 1991).

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the agents of the invention may be used to treat diseases mediated by modulation or regulation of protein kinases. An "effective amount" is intended to mean that amount of an agent that, when administered to a mammal in need of such treatment, is sufficient to effect treatment for a disease mediated by the activity of one or more protein kinases, such as tryosine kinases. Thus, e.g., a therapeutically effective amount of a compound of the Formula I, salt, active metabolite or prodrug thereof is a quantity sufficient to modulate, regulate, or inhibit the activity of one or more protein kinases such that a disease condition which is mediated by that activity is reduced or alleviated.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art. "Treating" is intended to mean at least the mitigation of a disease condition in a mammal, such as a human, that is affected, at least in part, by the activity of one or more protein kinases, such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The inventive agents may be prepared using the reaction routes and synthesis schemes as described below, employing the techniques available in the art using starting materials that are readily available.

In one general synthetic process, compounds of Formula I are prepared according to the following reaction scheme:

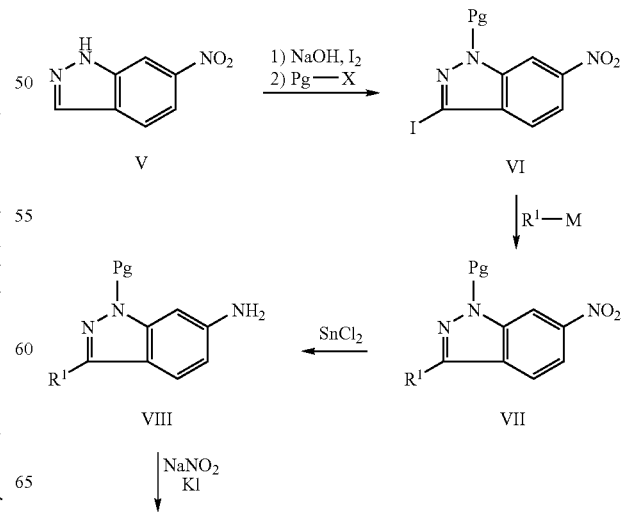

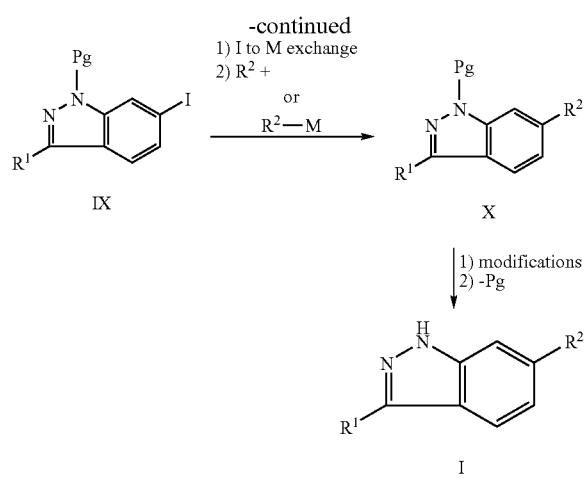

6-Nitroindazole (compound V) is treated with iodine and base, e.g., NaOH, in an aqueous/organic mixture, preferably with dioxane. The mixture is acidified and the product isolated by filtration. To the resulting 3-iodo-6-nitroindazole in dichloromethane-50% 5 aqueous KOH at 0° C. is added a protecting group ("Pg") reagent (wherein X=halo), preferably trimethylsilylethoxymethyl chloride (SEM-CL), and a phase transfer catalyst, e.g., tetrabutylammonium bromide (TBABr). After 1–4 hours, the two phases are diluted, the organics are separated, dried with sodium sulfate, filtered and concentrated. The crude product is purified by silica gel chromatography to give compounds of formula VI. Treatment of compounds of formula VI in a suitable organic solvent with a suitable $R^1$-organometallic reagent, preferably an $R^1$-boronic acid, in the presence of aqueous base, e.g., sodium carbonate, and a suitable catalyst, preferably Pd(PPh$_3$)$_4$ gives, after extractive work-up and silica gel chromatography, compounds of formula VII. The $R^1$ substituent may be exchanged within compounds of formula VII or later intermediates throughout this scheme by oxidative cleavage (e.g., ozonolysis) followed by additions to the resulting aldehyde functionality with Wittig or condensation transformations (typified in Example 42(a–e)). Treatment of compounds of formula VII with a reducing agent, preferably SnCl$_2$, provides, after conventional aqueous work up and purification, compounds of formula VIII. For the series of derivatives where Y=NH or N-lower alkyl, compounds of formula VIII may be treated with aryl or heteroaryl chlorides, bromides, iodides or triflates in the presence of a base, preferably Cs$_2$CO$_3$, and catalyst, preferably Pd-BINAP, (and where Y=N-lower alkyl, with a subsequent alkylation step) to provide compounds of formula X. To produce other Y linkages, sodium nitrite is added to compounds of formula VIII under chilled standard aqueous acidic conditions followed by the addition of potassium iodide and gentle warming. Standard work-up and purification produces iodide compounds of formula IX.

Treatment of compounds of formula IX with an organometallic reagent, e.g., butyllithium, promotes lithium halogen exchange. This intermediate is then reacted with an $R^2$ electrophile, e.g., a carbonyl or triflate, through the possible mediation of additional metals and catalysts, preferably zinc chloride and Pd(PPh$_3$)$_4$ to provide compounds of formula X. Alternatively, compounds of formula IX may be treated with an organometallic reagent such as an organoboronic acid in the presence of a catalyst, e.g., Pd(PPh$_3$)$_4$, under a carbon monoxide atmosphere to give compounds of formula X. Alternatively, for derivatives where Y=NH or S, compounds of formula IX may be treated with appropriate amines or thiols in the presence of base, preferably Cs$_2$CO$_3$ or K$_3$PO$_4$ and a catalyst, preferably Pd-BINAP or Pd-(bis-cyclohexyl)biphenylphosphine to provide compounds of formula X. Conventional functional group interchanges, such as oxidations, reductions, alkylations, acylations, condensations, and deprotections may then be employed to further derivatize this series giving final compounds of Formula I.

The inventive compounds of Formula I may also be prepared according general procedure shown in the following scheme:

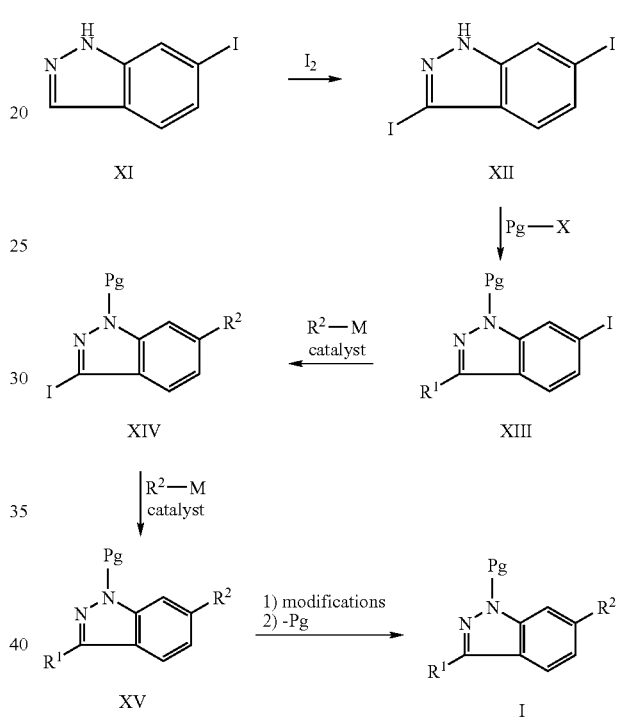

6-Iodoindazole (XI) is treated with iodine and base, e.g., NAOH, in an aqueous/organic mixture, preferably with dioxane. The mixture is acidified and the product XII is isolated by filtration. To the resulting 3,6 di-iodoindazole in dichloromethane-50% aqueous KOH at 0° C. is added a protecting group reagent, preferably SEM-Cl, and a phase transfer catalyst, e.g., TBABr. The two phases are diluted, the organics separated, dried with sodium sulfate, filtered and concentrated. The crude product is purified by silica gel chromatography to give compounds of the formula XII. Treatment of compounds of formula XII in a suitable organic solvent with a suitable $R^2$-organometallic reagent, e.g., $R^2$—ZnCl or boron $R^2$-boron reagent and a suitable catalyst, preferably Pd(PPh$_3$)$_4$ gives, after extractive work-up and silica gel chromatography, compounds of formula XIV. Treatment of compounds of formula XIV in a suitable organic solvent with a suitable $R^1$-organometallic reagent (e.g., boron $R^1$-boron reagent or $R^1$—ZnCl), in the presence of aqueous base, sodium carbonate, and a suitable catalyst, preferably Pd(PPh$_3$)$_4$ gives, after extractive work-up and silica gel chromatography, compounds of formula XV. Conventional functional group interchanges, such as oxidations, reductions, alkylations, acylations, condensations and deprotections may then be employed to further derivatize this series giving final compounds of Formula I.

Alternatively, compounds of Formula I where $R^2$ is a substituted or unsubstituted Y—Ar, where Y is O or S may be prepared according to the following general scheme:

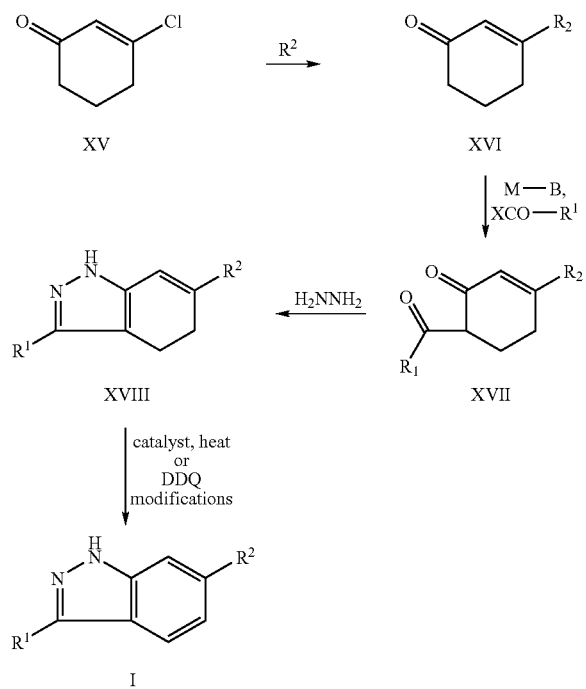

A stirred acetone solution of 3-chloro-cyclohex-2-enone (XV), H—$R^2$, and anhydrous potassium carbonate is refluxed for 15–24 hours, cooled, and filtered. Concentrating and chromatographing the filtrate on silica gel gives 3-$R^2$-cyclohex-2-enone (XVI).

The ketones of formula XVI may be reacted with a suitable base (M-B), preferably lithium bis(trimethylsily) amide, and reacted with $R^1$—CO—X (where X=halogen), which after standard acid work up and purification provides compounds of the formula XVII. This product, in HOAc/EtOH, combined with hydrazine monohydrate, is heated at a suitable temperature for an appropriate time period, preferably at 60–80° C. for 2–4 hours. After cooling, the mixture is poured into saturated sodium bicarbonate solution, extracted with an organic solvent, concentrated, and purified on silica gel to give compounds of formula XVIII. Compounds of formula XVIII may be oxidized using a variety of known methods to give compounds of the Formula I.

Other compounds of Formula I may be prepared in manners analogous to the general procedures described above or the detailed procedures described in the examples herein. The affinity of the compounds of the invention for a receptor may be enhanced by providing multiple copies of the ligand in close proximity, preferably using a scaffolding provided by a carrier moiety. It has been shown that provision of such multiple valence compounds with optimal spacing between the moieties dramatically improves binding to a receptor. See, e.g., Lee et al., Biochem, 23, 4255 (1984). The multivalency and spacing can be controlled by selection of a suitable carrier moiety or linker units. Such moieties include molecular supports which contain a multiplicity of functional groups that can be reacted with functional groups associated with the compounds of the invention. Of course, a variety of carriers can be used, including proteins such as BSA or HAS, a multiplicity of peptides including, for example, pentapeptides, decapeptides, pentadecapeptides, and the like. The peptides or proteins can contain the desired number of amino acid residues having free amino groups in their side chains; however, other functional groups, such as sulfhydryl groups or hydroxyl groups, can also be used to obtain stable linkages.

Compounds that potently regulate, modulate, or inhibit the protein kinase activity associated with receptors VEGF, FGF, CDK complexes, TEK, CHK1, LCK, FAK, and phosphorylase kinase among others, and which inhibit angiogenesis and/or cellular profileration is desirable and is one preferred embodiment of the present invention. The present invention is further directed to methods of modulating or inhibiting protein kinase activity, for example in mammalian tissue, by administering an inventive agent. The activity of the inventive compounds as modulators of protein kinase activity, such as the activity of kinases, may be measured by any of the methods available to those skilled in the art, including in vivo and/or in vitro assays. Examples of suitable assays for activity measurements include those described in Parast C. et al., BioChemistry, 37, 16788–16801 (1998); Jeffrey et al., Nature, 376, 313–320 (1995); WIPO International Publication No. WO 97/34876; and WIPO International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I, II, III, or IV and an inert, pharmaceutically acceptable carrier or diluent. In one embodiment of the pharmaceutical compositions, efficacious levels of the inventive agents are provided so as to provide therapeutic benefits involving modulation of protein kinases. By "efficacious levels" is meant levels in which the effects of protein kinases are, at a minimum, regulated. These compositions are prepared in unit-dosage form appropriate for the mode of administration, e.g., parenteral or oral administration.

An inventive agent is administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent is dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, gylcerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, more preferably from about 0.001 to about 50 mg/kg body weight, with courses of treatment repeated at appropriate intervals. Administration of prodrugs are typically dosed at weight levels which are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For administration to the eye, a compound of the Formula I, II, III, or IV is delivered in a pharmaceutically acceptable ophthalmic vehicle such that the compound is maintained in contact with the ocular surface for a sufficient time period to allow the compound to penetrate the corneal and internal regions of the eye, including, for example, the anterior chamber, posterior chamber, vitreous body, aqueous humor, vitreous humor, cornea, iris/cilary, lens, choroid/retina and selera. The pharmaceutically acceptable ophthalmic vehicle may be an ointment, vegetable oil, or an encapsulating material. A compound of the invention may also be injected directly into the vitreous and aqueous humor.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

A pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The preparation of preferred compounds of the present invention is described in detail in the following examples, but the artisan will recognize that the chemical reactions described may be readily adapted to prepare a number of other protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or known in the art will be recognized as having applicability for preparing other compounds of the invention.

EXAMPLES

The exemplary compounds described above may be formulated into pharmaceutical compositions according to the following general examples.

Example 1

Parenteral Composition

To prepare a parenteral pharmaceutical composition suitable for administration by injection, 100 mg of a water-soluble salt of a compound of Formula I is dissolved in DMSO and then mixed with 10 mL of 0.9% sterile saline. The mixture is incorporated into a dosage unit form suitable for administration by injection.

Example 2

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

Example 3

Intraocular Composition

To prepare a sustained-release pharmaceutical composition for intraocular delivery, a compound of Formula I is suspended in a neutral, isotonic solution of hyaluronic acid (1.5% conc.) in phosphate buffer (pH 7.4) to form a 1% suspension.

Example 4

Inhibition of Circulating Endothelial Progenitors (CEP)

Here we report the efficacy of a particular compound of formula I, 6-[2-(methylcarbamoyl)phenylsulfanyl]-3-E-[2-(pyridin-2-yl)ethenyl]indazole, represented by formula A and denoted "Compound A"

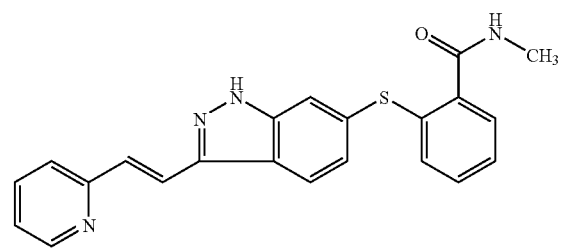

in our high-grade lymphoma model (orthotopic ip injection of Namalwa cells in NOD/SCID mice, Bertolini et al., Blood 2000). Daily administration of Compound A was associated with a significant delay of lymphoma onset and reduction of lymphoma growth in comparison to untreated controls mice (p<0.0001) and mice treated with the maximum tolerable dose (MTD) of cyclophosphamide (CTX, p<0.01). Compound A activity peaked at 30 mg/kg/day. Mice treated with a maximum tolerable dose of CTX, daily Compound A or PBS as a control and were evaluated every 5 days for the presence of mature circulating endothelial cells (CEC) and circulating endothelial progenitors (CEP), two novel surrogate markers of angiogenesis and vasculogenesis. CECs were enumerated as CD45VEGFR2/CD13$^+$ cells, and the CEP subset was enumerated as CD45VEGFR2/CD13$^+$ CD117$^+$ cells. CEC and CEP viability was evaluated by 7MD staining (Monestiroli et al., *Cancer Res* 2001).

In lymphoma-bearing mice, the first course of MTD CTX delayed but did not prevent tumor growth, and a dramatic increase in CEP number and viability was observed a few days after MTD CTX. This CEP mobilization wave was not due solely to tumor growth, because its magnitude was significantly higher than that observed in control animals, which, at the same time, already had significantly larger tumors. In MTD CTX-treated animals, the subsequent courses of MTD CTX did not reduce tumor growth. Conversely, when MTD CTX-treated animals were given daily Compound A, CEP mobilization was significantly down-regulated and both CEP viability and tumor recurrence were significantly reduced (p<0.001). Taken together, the data indicate that Compound A has activity in lymphoma and reduces the mobilizaton of CEP associated with the MTD of CTX. Thus, in addition to anti-lymphoma activity, this drug appears to be a promising candidate for sequential use after high-dose chemotherapy in order to suppress CEP mobilization.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A method of treating a hyperproliferative disorder in a mammal, the method comprising administering to said mammal a therapeutically effective amount of a composition comprising a compound of formula I:

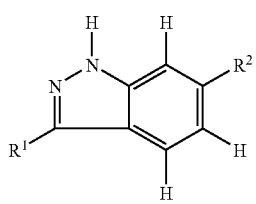

wherein:
R$^1$ is a substituted or unsubstituted aryl or heteroaryl, or a group of the formula CH=CH—R$^3$ or CH=N—R$^3$ where R$^3$ is a substituted or unsubstituted alkyl, alkenyl, cycloalkyl, heterocycloalkyl, aryl, or heteroaryl; and R$^2$ is a substituted or unsubstituted aryl, heteroaryl, or Y—X, where Y is O, S, C=CH$_2$, C=O, S=O, SO$_2$, alkylidene, NH, or N—(C$_1$-C$_8$ alkyl), and X is substituted or unsubstituted Ar, heteroaryl, NH-(alkyl), NH-(cycloalkyl), NH-(heterocycloalkyl), NH(aryl), NH(heteroaryl), NH-(alkoxyl), or NH-(dialkylamide);

or pharmaceutically acceptable prodrugs, pharmaceutically active metabolites, and pharmaceutically acceptable salts thereof, and a pharmaceutically acceptable carrier.

2. The method of claim 1, wherein said hyperproliferative disorder is cancer.

3. The method of claim 2, wherein the cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, and combinations thereof.

4. The method of claim 1, wherein said hyperproliferative disorder is a noncancerous hyperproliferative disorder.

5. The method of claim 4, wherein said noncancerous hyperproliferative disorder is a benign hyperplasia of the skin or prostate.

6. The method of claim 1, further comprising administering to the mammal an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antibodies, cytotoxics, anti-hormones, anti-androgens, and mixtures thereof.

7. A method for treating a disease related to vasculogenesis or angiogenesis in a mammal, the method comprising administering to said mammal a therapeutically effective amount of a composition comprising a compound of formula I:

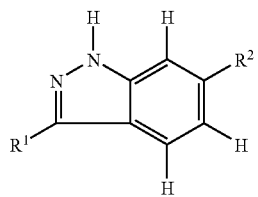

wherein:
R$^1$ is a substituted or unsubstituted aryl or heteroaryl, or a group of the formula CH=CH—R$^3$ or CH=N—R$^3$ where R$^3$ is a substituted or unsubstituted alkyl, alkenyl, cycloalkyl, heterocycloalkyl, aryl, or heteroaryl; and R² is a substituted or unsubstituted aryl, heteroaryl, or Y—X, where Y is O, S, C=CH₂, C=O, S=O, SO₂, alkylidene, NH, or N—(C₁–C₈ alkyl), and X is substituted or unsubstituted Ar, heteroaryl, NH-(alkyl), NH-(cycloalkyl), NH-(heterocycloalkyl), NH(aryl), NH(heteroaryl), NH-(alkoxyl), or NH—(dialkylamide);

or pharmaceutically acceptable prodrugs, pharmaceutically active metabolites, and pharmaceutically acceptable salts thereof, and a pharmaceutically acceptable carrier.

8. The method of claim 7, wherein said disease is selected from the group consisting of tumor angiogenesis, hemangioma, glioma, melanoma, Kaposi's sarcoma and ovarian, breast, lung, pancreatic, prostate, colon and epidermoid cancer.

9. The method of claim 7, further comprising administering to the mammal a therapeutically effective amount of an anti-hypertensive agent.

10. A method according to claim 1, wherein said compound of formula I is selected from the group consisting of:

11. A method according to claim 7, wherein said compound of formula I is selected from the group consisting of:

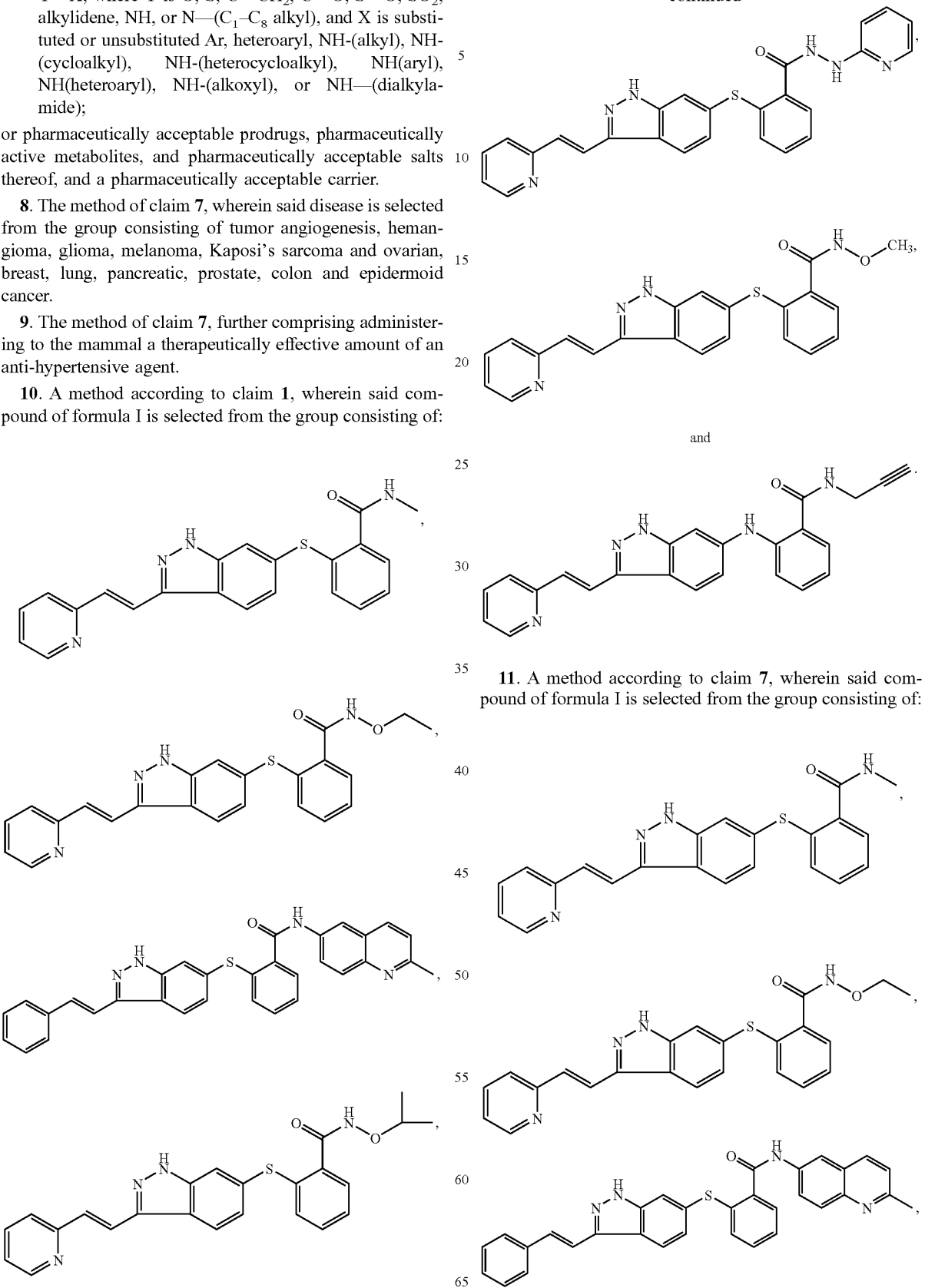

-continued
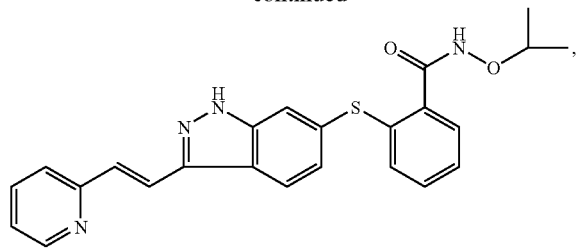
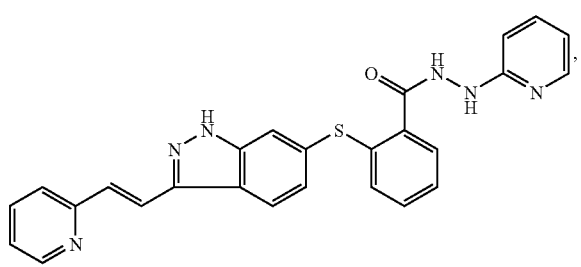
-continued
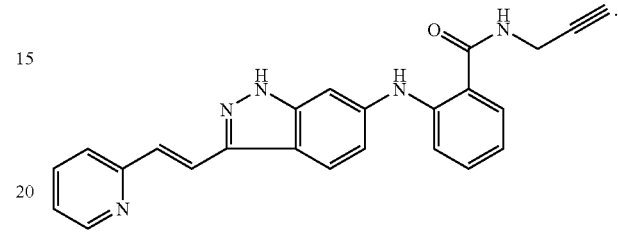
and
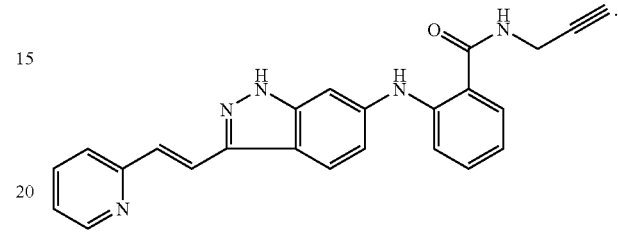
* * * * *